United States Patent
Hyun et al.

(10) Patent No.: US 9,642,590 B2
(45) Date of Patent: May 9, 2017

(54) ADAPTIVE COLOR DOPPLER IMAGE FORMATION

(75) Inventors: Dong Gyu Hyun, Seoul (KR); Jong Sik Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 842 days.

(21) Appl. No.: 12/547,178

(22) Filed: Aug. 25, 2009

(65) Prior Publication Data

US 2010/0056923 A1    Mar. 4, 2010

(30) Foreign Application Priority Data

Aug. 27, 2008    (KR) .................. 10-2008-0083726

(51) Int. Cl.
| | | |
|---|---|---|
| A61B 8/00 | (2006.01) | |
| A61B 8/06 | (2006.01) | |
| G01S 7/52 | (2006.01) | |
| G01S 15/89 | (2006.01) | |

(52) U.S. Cl.
CPC .............. *A61B 8/06* (2013.01); *A61B 8/463* (2013.01); *A61B 8/54* (2013.01); *A61B 8/585* (2013.01); *G01S 7/52085* (2013.01); *G01S 15/8979* (2013.01)

(58) Field of Classification Search
CPC .................................. A61B 8/585; A61B 8/08
USPC .......... 600/454, 440–441, 447, 453, 455–457
See application file for complete search history.

(56) References Cited

U.S. PATENT DOCUMENTS

| | | | |
|---|---|---|---|
| 4,817,619 A | | 4/1989 | Sugiyama |
| 5,961,462 A | * | 10/1999 | Loupas et al. ............... 600/453 |
| 6,682,483 B1 | * | 1/2004 | Abend ............... G01S 7/52026 |
| | | | 128/916 |
| 2003/0018264 A1 | | 1/2003 | Suzuki et al. |
| 2006/0100515 A1 | | 5/2006 | Nakata |
| 2006/0116578 A1 | * | 6/2006 | Grunwald et al. ............ 600/440 |

FOREIGN PATENT DOCUMENTS

| | | |
|---|---|---|
| JP | 62-90144 A | 4/1987 |
| JP | 02-142545 A | 5/1990 |
| JP | 05-049639 | 3/1993 |
| JP | 06-269453 A | 9/1994 |
| JP | 07-178086 A | 7/1995 |
| JP | 10-033535 A | 2/1998 |
| JP | 2003-010182 A | 1/2003 |

(Continued)

OTHER PUBLICATIONS

Korean Office Action issued in Korean Patent Application No. KR 10-2008-0083726 dated Feb. 10, 2011.

(Continued)

*Primary Examiner* — Joel Lamprecht
(74) *Attorney, Agent, or Firm* — McDermott Will & Emery LLP (57) ABSTRACT

Embodiments for adaptively forming color Doppler images in an ultrasound diagnostic system are disclosed. A method of forming a color Doppler image in an ultrasound diagnostic system comprises: scanning a first set of scan lines set at a full scan region to detect at least one scan line that passes a moving object in the full scan region among the first set of scan lines; setting a second set of scan lines based on the detected scan lines; and scanning the second set of scan lines to form a first color Doppler image.

14 Claims, 8 Drawing Sheets

(56) References Cited

FOREIGN PATENT DOCUMENTS

| | | |
|---|---|---|
| JP | 2005253852 A | 9/2005 |
| JP | 2008012141 A | 1/2008 |
| KR | 10-2002-0096965 | 12/2002 |
| KR | 10-2005-0084366 | 8/2005 |
| WO | WO 2004/054448 A1 | 7/2004 |
| WO | WO 2006/138185 A2 | 12/2006 |

OTHER PUBLICATIONS

Extended European Search Report for Patent Application No. 09167958.9-2319, mailed Oct. 22, 2009, 6 pages.
Korean Office Action issued in Korean Patent Application No. KR 10-2008-0083726 dated Nov. 30, 2011.
Japanese Office Action with Full English Translation issued in Japanese Patent Application No. 2009-194355 mailed Sep. 24, 2013.
European Office Action issued in European Patent Application No. 09 167 958.9 dated Apr. 14, 2014.
Japanese Office Action issued in Japanese Patent Application No. 2009-194355 dated Apr. 8, 2014, with English Translation.

\* cited by examiner

ADAPTIVE COLOR DOPPLER IMAGE FORMATION

The present application claims priority from Korean Patent Application No. 10-2008-0083726 filed on Aug. 27, 2008, the entire subject matter of which is incorporated herein by reference.

TECHNICAL FIELD

The present disclosure generally relates to ultrasound systems, and more particularly to an adaptive color Doppler image formation in an ultrasound diagnostic system.

BACKGROUND

Recently, an ultrasound system has been used extensively in the medical field due to its non-invasive and non-destructive nature. Modern high-performance ultrasound imaging systems and techniques are commonly used to produce two-dimensional ultrasound images and three-dimensional ultrasound images of internal features of patients.

Generally, the ultrasound system may provide a color Doppler mode, wherein color Doppler images may be obtained. The color Doppler images may visualize velocities and directions of moving objects in a target object by using Doppler shift. The color Doppler images may be represented by various colors, which indicate velocities and directions of moving objects (e.g., heart) or blood flows within blood vessels. In the color Doppler image, for example, the blood flow approaching toward an ultrasound probe may be represented by a red color, while the blood flow moving away from the ultrasound probe may be represented by a blue color. Further, the blood flow of a relatively high speed may be represented by a light color, while the blood flow of a relatively slow speed may be represented by a dark color.

However, when a conventional diagnostic system operates in a color Doppler mode to obtain color Doppler images for a full scan region (e.g., 256 scan lines) in a typical depth (shown in FIG. 1), there is a problem in that the color Doppler images are obtained at a relatively low frame rate of about 1-2 frames/second due to the physical speed limitation of ultrasound signals.

SUMMARY

Embodiments for forming a color Doppler image at an enhanced frame rate are disclosed herein. In one embodiment, by way of non-limiting example, a method of forming a color Doppler image in an ultrasound diagnostic system comprises: scanning a first set of scan lines set at a full scan region to detect at least one scan line that passes a moving object in the full scan region among the first set of scan lines; setting a second set of scan lines based on the detected scan lines; and scanning the second set of scan lines to form a first color Doppler image.

In another embodiment, an ultrasound diagnostic system comprises: a probe operable to transmit ultrasound signals into a target object and receive echo signals reflected from the target object to thereby output receive signals, the receive signals including first receive signals obtained by scanning a first set of scan lines set at a full scan region; and an image processing unit operable to detect at least one scan line that passes a moving object in the full scan region among the first set of scan lines based on the first receive signals, the image processing unit being operable to set a second set of scan lines based on the detected scan lines, wherein the probe is operable to scan the second set of scan lines to thereby output second receive signals, and wherein the image processing unit is further operable to form a first color Doppler image based on the second receive signals.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 2:
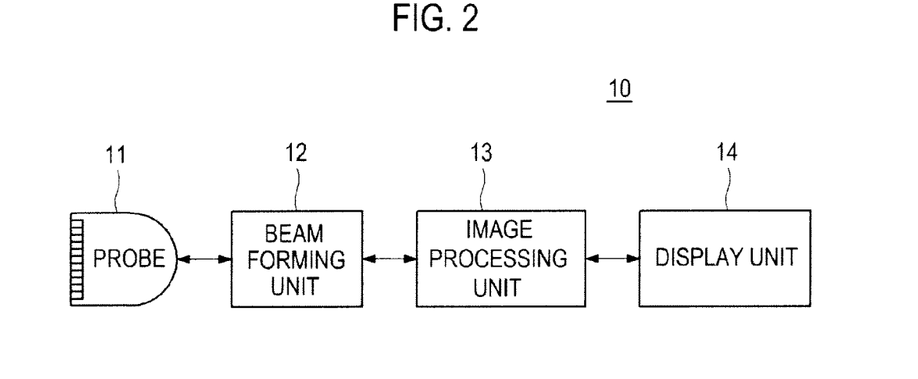
FIG. 2 is a block diagram showing an illustrative embodiment of an ultrasound diagnostic system.

FIG. 2 is a block diagram showing an illustrative embodiment of an ultrasound diagnostic system. Referring to FIG. 2, the ultrasound diagnostic system 10 may include a probe 11, a beam forming unit 12, an image processing unit 13 and a display unit 14. The ultrasound diagnostic system 10 will be described below in terms of its operation in color Doppler mode. The color Doppler mode may include a velocity mode, a power mode, a variance mode, a power Doppler mode, a 3D power Doppler mode and the like.

The probe 11 may include an array transducer having a plurality of transducer elements for converting electrical pulse signals into ultrasound signals, and vice-versa. In one embodiment, the array transducer may include a 1-dimensional or 2-dimensional array transducer. The probe 11 may be operable to transmit ultrasound signals into a target object in response to electrical pulse signals. It then receives echo signals reflected from the target object. The transducer elements may be operable to convert the echo signals into electrical receive signals. In one embodiment, the electrical receive signals may include first receive signals obtained by scanning a first set of scan lines and second receive signals obtained by scanning a second set of scan lines. The first set of scan lines may be set to scan a full scan region with a first scan line density, while the second set of scan lines may be set to scan a specific part of scan region with a second scan line density. In one embodiment, the second scan line density may be set to be greater than the first scan line density. The setting of the first and second sets of scan lines will be described later in detail. The probe 11 may further include an amplifier (not shown) that may be operable to amplify the electrical receive signals outputted from the transducer elements.

The beam forming unit 12 may be coupled to the probe 11 to thereby receive the first and second receive signals, which may be amplified by the amplifier. The beam forming unit 12 may be operable to apply delays to the receive signals in consideration of distances between the transducer elements and focal points to thereby output receive-focused beams.

The image processing unit 13 may be coupled to the beam forming unit 12 to thereby receive the receive-focused beams. The image processing unit 13 may be operable to form a plurality of color Doppler image frames based on the receive-focused beams. The color Doppler image frames may include a first color Doppler image frame formed based on the first receive signals (hereinafter referred to as "scanning frame") and a second color Doppler image frame formed based on the second receive signals (hereinafter referred to as "adaptive frame"). The image processing unit 13 may be further operable to compound the scanning frame and the adaptive frame to thereby form a compound image frame.

The display unit 14 may be coupled to the processing unit 13. The display unit 14 may display the scanning frame image, the adaptive image frame or the compound image frame. The display unit 14 may include CRT monitor, LCD monitor or the like.

Hereinafter, various embodiments for setting the first and second sets of scan lines will be described in detail with reference to FIGS. 3 to 12. In one embodiment, the first set of scan lines may be set to detect blood flow regions (or blood vessel regions) in the full scan region, while the second set of scan lines may be set to scan at least one blood flow region (or blood vessel regions). The setting of the second set of scan lines may adaptively vary depending on the detection result of the blood flow during the scanning of the first set of scan lines. The scanning may be carried out by transmitting a transmit beam along each of the scan lines as many as a predetermined ensemble number (or packet number) and receiving echo signals. The detection of the blood flow may be implemented by detecting a Doppler shift frequency from the echo signals and comparing the Doppler shift frequency with a threshold. For example, if the detected Doppler shift frequency is greater than the threshold, then it may be determined that the blood flows exist. Otherwise, it may be determined that the blood flows do not exist. In one embodiment, a wide width of a transmit beam for scanning the first set of scan lines may be used to prevent errors upon occurrence of which the blood flow regions, which are in fact existent, are not detected. Also, a multi beam or a flat beam may be used as the transmit beam for scanning the first set of scan lines. Further, a zone beam forming may be utilized.

The second set of scan lines may be set based on the scan lines on which the blood flow is detected among the first set of scan lines. For example, if the blood flow is detected on the specific scan lines among the first set of scan lines, then the second set of scan lines may be set to include the specific scan lines and neighboring scan lines thereof. In such a case, the neighboring scan lines may be set by a part of the first set of scan lines or newly set to be denser than the first scan lines.

Figure 3:
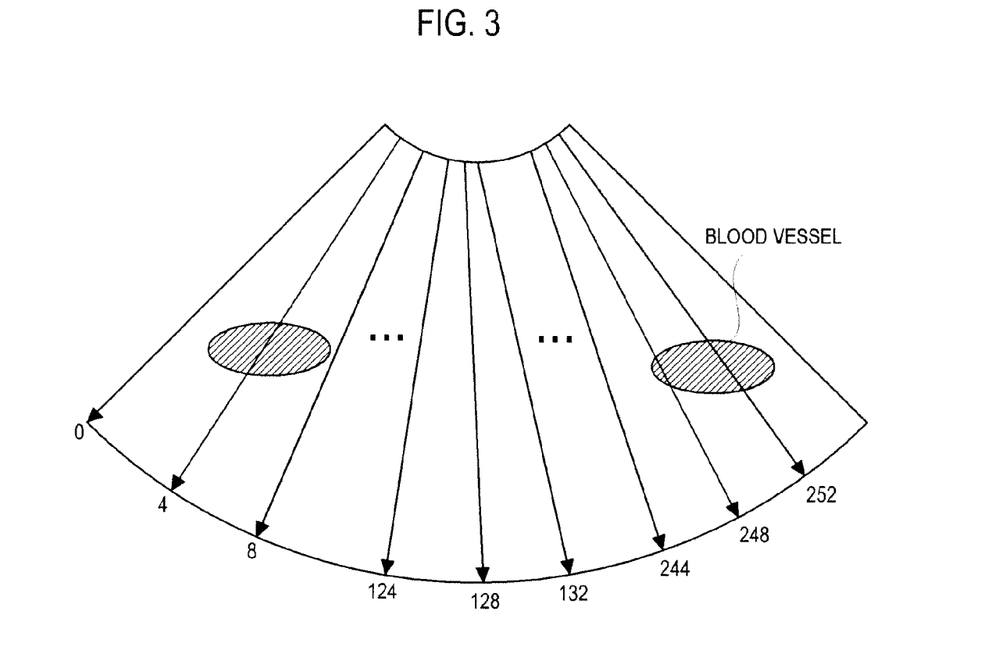
FIG. 3 is a schematic diagram showing an example of setting scan lines for a scanning frame.

In one embodiment, assuming that scan lines, which are indexed by 0-255, are typically set to obtain color Doppler images in the color Doppler mode, the first set of scan lines may be uniformly set at a predetermined scan line interval. The scan line interval may be set to "1," "2," "4," "8," "6," "32" and the like. For example, when the scan line interval is set to "4," the first set of scan lines may be set by using scan lines 0, 4, 8-244, 248 and 252 among the scan lines 0-255, as shown in FIG. 3. However, the scan line interval may not be limited thereto.

Figure 4:
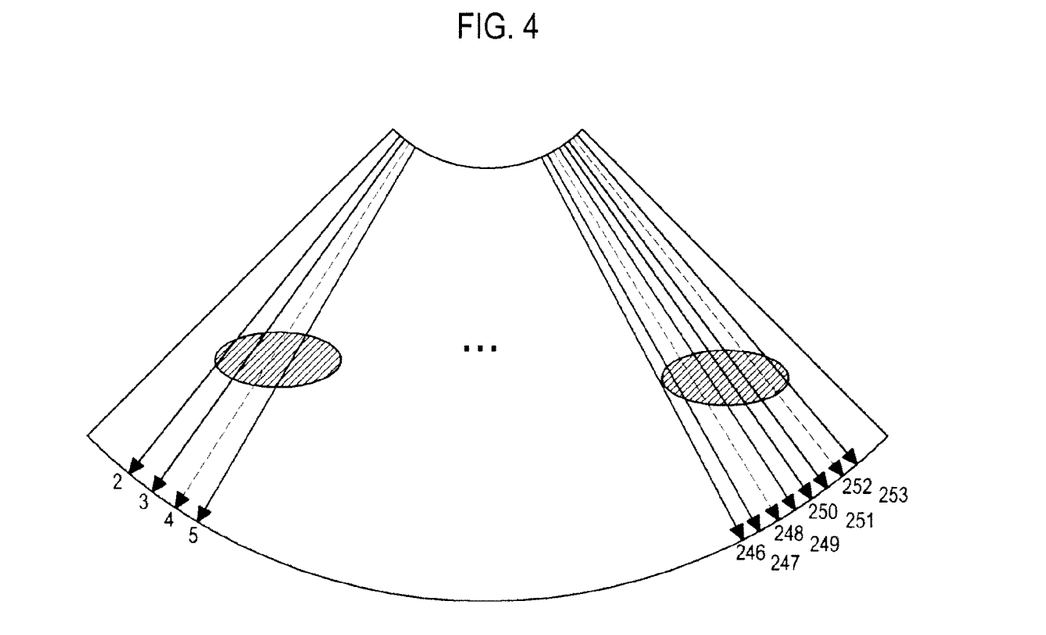
FIGS. 4-6 are schematic diagrams showing examples of setting scan lines for adaptive frames.

If the blood flows are detected on the scan lines 4, 248 and 252 while scanning the first set of the scan lines 0, 4, 8-244, 248 and 252 (as shown in FIG. 3), then the second set of scan lines may be set by using the scan lines 4, 248 and 252 and neighboring scan lines thereof. In such a case, the neighboring scan lines may be set to ±1 or ±2 scan lines away from the scan lines on which the blood flow is detected. However, the neighboring scan lines are not limited thereto. When the neighboring scan lines are set to ±1 scan lines away from the scan lines on which the blood flow is detected, the second set of scan lines may be set by using the scan lines 2-5 and 246-253, as shown in FIG. 4. Although it is described that the second set of scan lines is set to 12 scan lines (i.e., scan lines 2-5 and 246-253), the setting of the second set of scan lines is not limited thereto. The second set of scan lines may be set to be denser to have over 12 scan lines (e.g., 24, 36, 64 scan lines).

Although it is described that the interval between neighboring scan lines in the second set of scan lines is set to "1" as an example, the scan line interval is not limited thereto. In one embodiment, the scan line interval may be determined according to the scan line interval of the first set of scan lines or the width of the transmit beam. For example, the scan line interval of the second set of the scan lines may be set to half or quarter of the scan line interval of the first set of scan lines. In one embodiment, the width of the transmit beam for scanning the first set of scan lines may be set to be wider than that for scanning the second set of scan lines.

Figure 5:
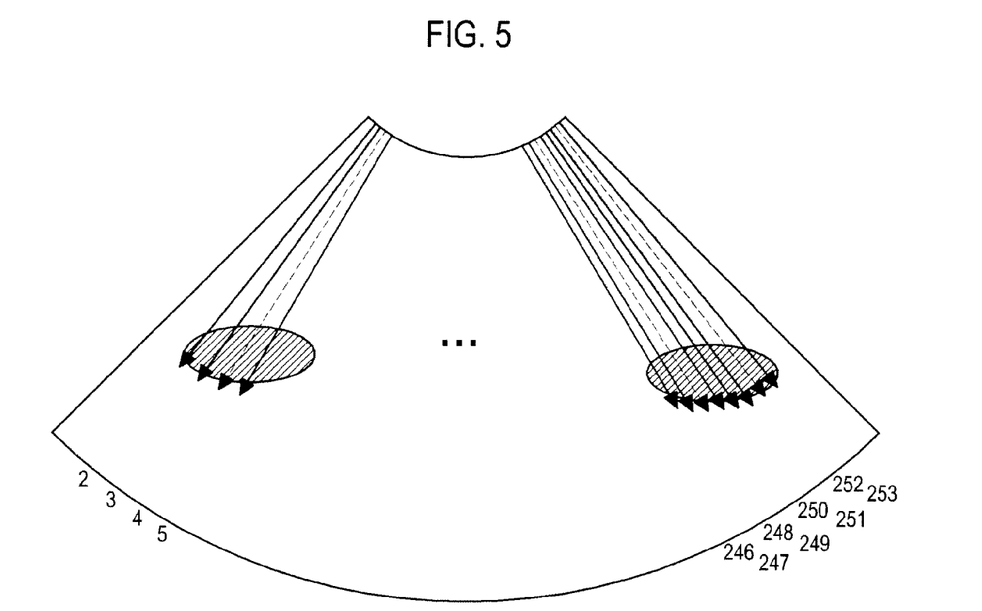
Figure 6:
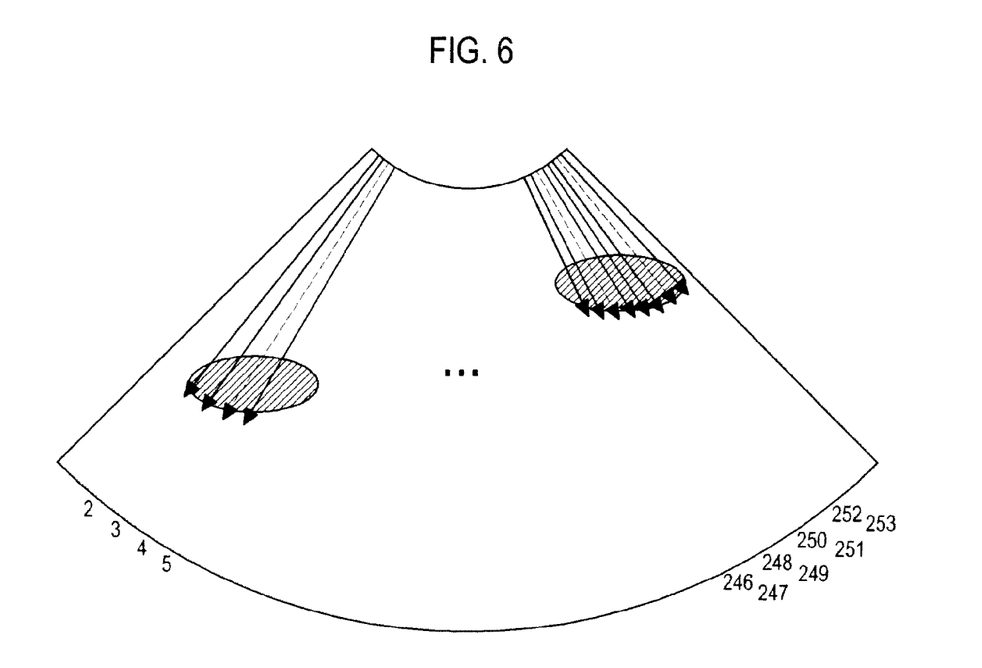

In one embodiment, the second set of scan lines may be set in consideration with the depths of the detected blood flows (or blood vessels). That is, the second set of scan lines may be set by different depths based on depths of the detected blood flows (or blood vessels), as shown in FIGS. 5 and 6. Thus, the scanning time for the second set of the scan line may be reduced so that the frame rate of the adaptive frame can be improved.

Figure 7:
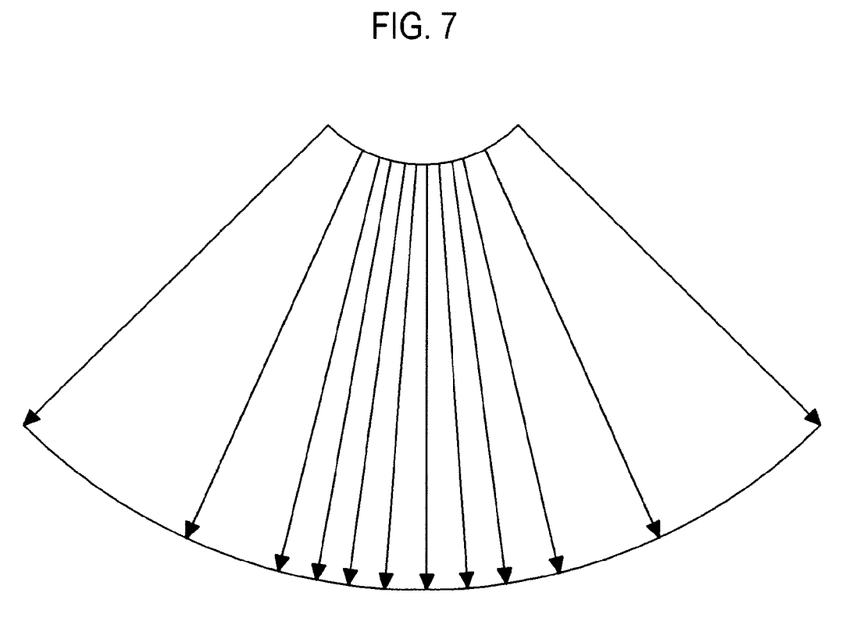
FIGS. 7 and 8 are schematic diagrams showing examples of setting scan lines for a scanning frame according to estimation of blood flows (blood vessels).
Figure 8:
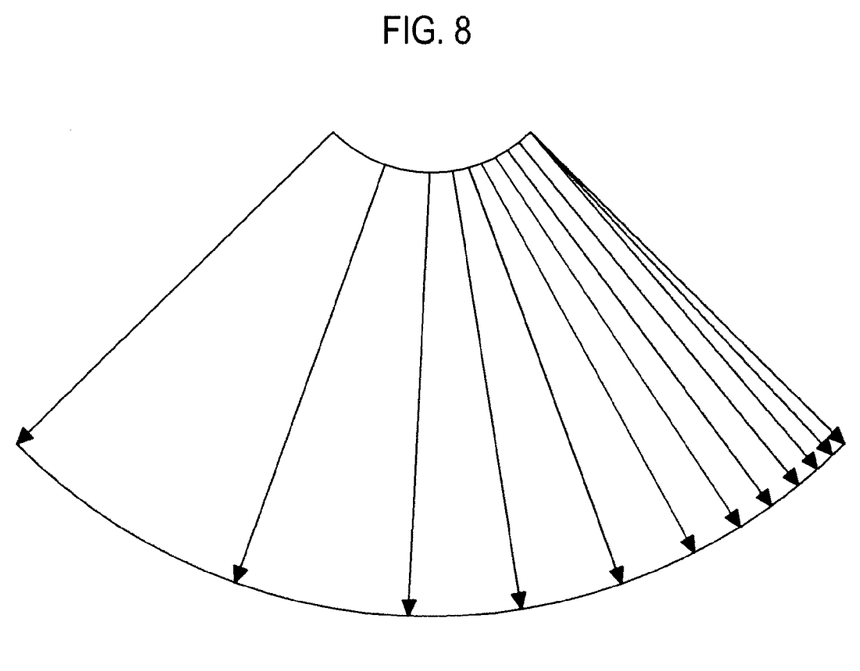
Figure 9:
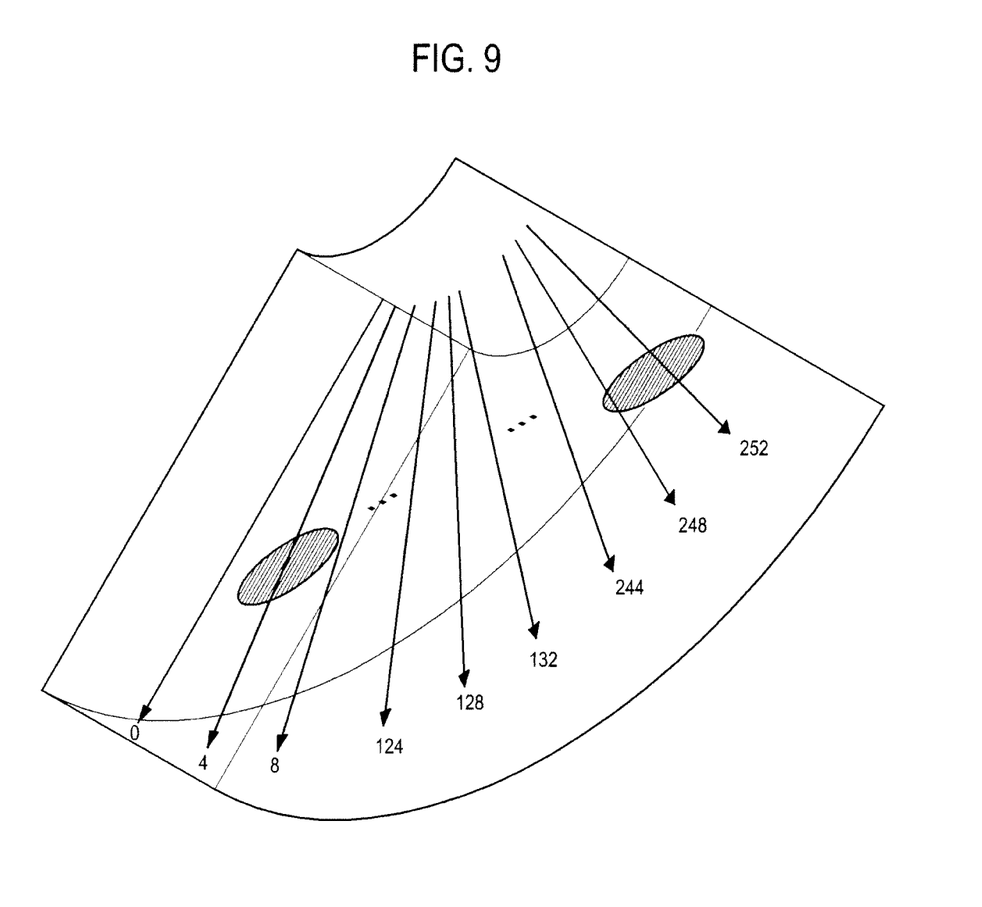
FIGS. 9-12 are schematic diagrams showing examples of setting scan lines for a scanning frame and an adaptive frame in a 3-dimensional space.
Figure 10:
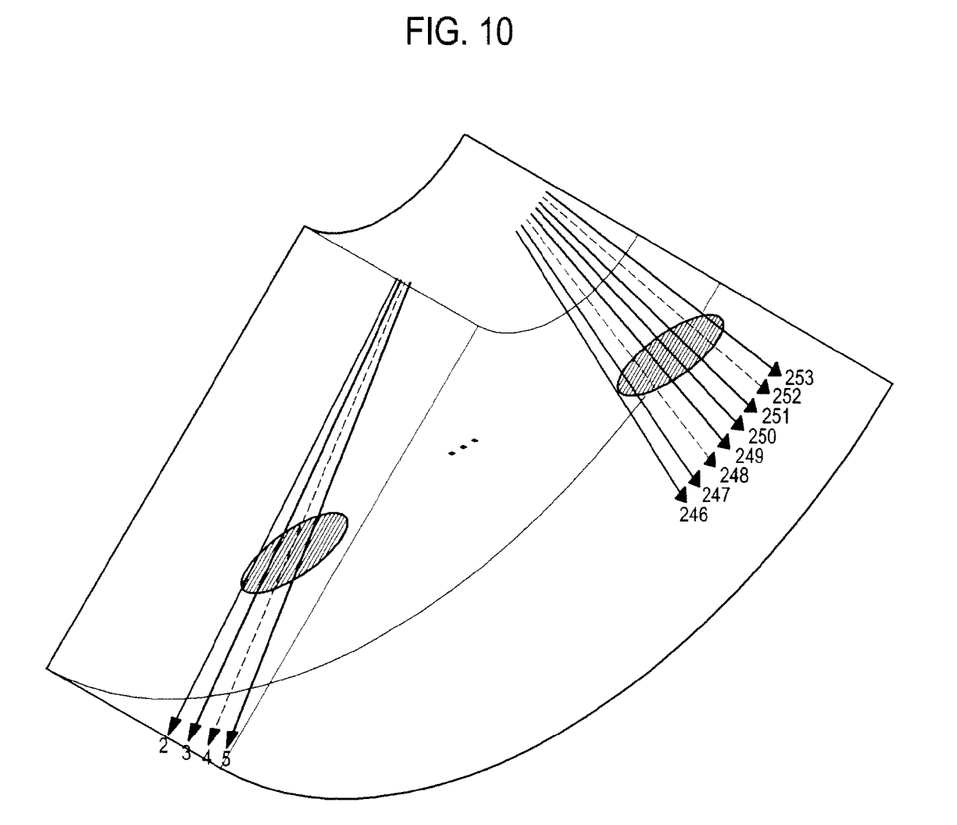
Figure 11:
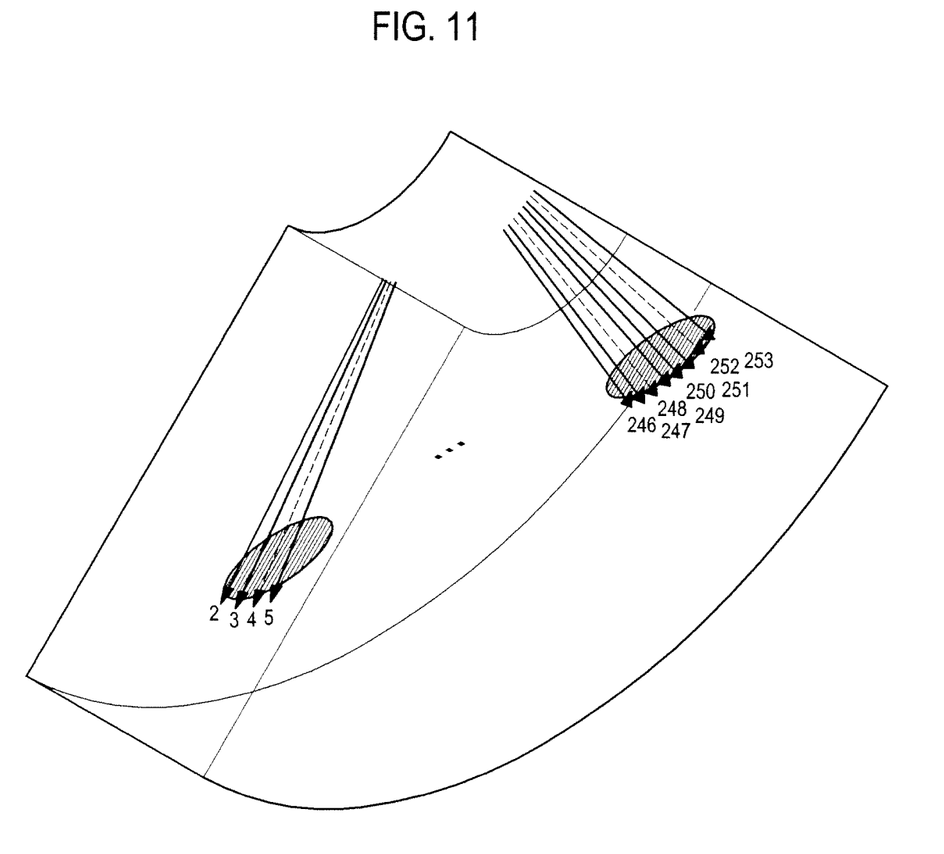
Figure 12:
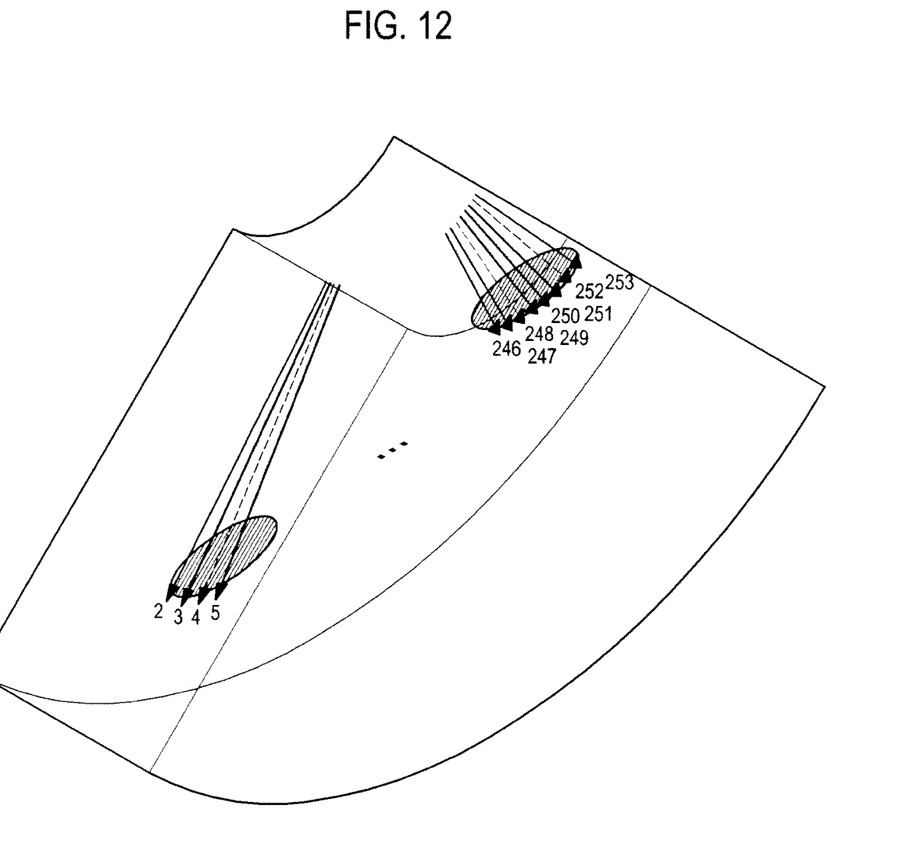

In one embodiment, the first set of scan line may be arbitrarily set according to possibility of the blood flow existence. If the possibility of the blood flow existence is relatively high or small blood vessels are expected to be relatively denser at a center portion of the scan region, or if large blood vessels are expected to be existent at left and right sides of the scan region, then the first set of scan lines may be set such that the scan lines at the center portion of the scan regions are denser than at both sides thereof, as shown in FIG. 7. Further, if the possibility of the blood flow existence is relatively high or small blood vessels are expected to be relatively dense at a right side of the scan region, or if large blood vessels are expected to be existent at a left side of the scan region, then the first set of scan lines may be set such that the scan lines at the right side thereof are denser than those at the left side thereof, as shown in FIG. 8.

Figure 1:
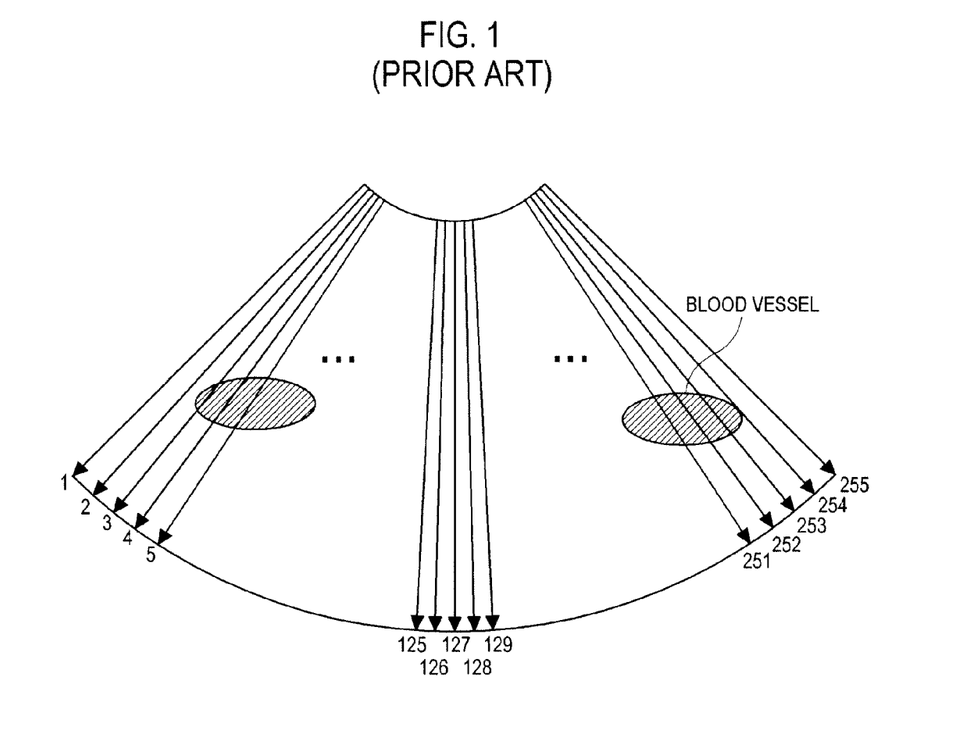
FIG. 1 is a schematic diagram showing a conventional scanning process of forming a color Doppler image for a full scan region.

In one embodiment, when the time necessary for obtaining one color Doppler image frame by scanning scan lines 0-255 as shown in FIG. 1 is "T," the frame rate is "F" and the first set of scan lines is set to quarter scan lines (i.e., 64 scan lines), the time necessary for obtaining a scanning frame may be 0.25T. Also, when the second set of scan lines is set to quarter scan lines (i.e., 64 scan lines), the time necessary for obtaining an adaptive frame may be 0.25T.

Assuming that the scanning frame is "A" and the adaptive frame is "B," the scanning frame and the adaptive frame may be alternately obtained in a manner of "ABAB . . . ." In such a case, the frame rate may be 2F. Also, if the scanning frame and the adaptive frame are obtained in a manner of "ABBBBBBBBBBABBBBBBBBBB . . . ," then the frame rate may be close to 4F.

In one embodiment, the setting of the first and second sets of the scan lines may be applied to scanning a region of interest for enhancement of the frame rate. Also, the setting of the first and second sets of the scan lines may be applied to a 3-dimensional space, as illustrated in FIGS. 9-12, to enhance the frame rate of the color Doppler image.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of forming a color Doppler image in an ultrasound diagnostic system, comprising:
   scanning a first set of scan lines at a full scan region to detect a moving object;
   determining a second set of scan lines, each of which passes the moving object from among the first set of scan lines, wherein the second set of scan lines includes a first scan line passing a first position in the moving object and a second scan line passing a second position in the moving object; and
   scanning the second set of scan lines and a predetermined number of scan lines neighboring to the second set of scan lines, exclusive of other scan lines,
   wherein the scanning the second set of scan lines comprises scanning the first scan line up to a first depth of the moving object at the first position and scanning the second scan line up to a second depth of the moving object at the second position, to form a first color Doppler image, the first depth and the second depth being different to each other depending on the first position and the second position in the moving object.

2. The method of claim 1, wherein the moving objects include a blood flow and a blood vessel.

3. The method of claim 1, further comprising forming a second color Doppler image based on the scanning of the first set of scan lines.

4. The method of claim 1, wherein the second set of scan lines is denser than the first set of scan lines.

5. The method of claim 1, wherein the first set of scan lines is set to have a uniform scan line density.

6. The method of claim 1, wherein the first set of scan lines is set with different scan line densities.

7. The method of claim 6, wherein the first set of scan lines is set based on a possibility of existence of the moving object.

8. An ultrasound diagnostic system, comprising:
   a probe configured to transmit ultrasound signals into a target object and receive echo signals reflected from the target object to thereby output receive signals, the receive signals including first receive signals obtained by scanning a first set of scan lines at a full scan region; and
   an image processor configured to:
      detect a moving object based on the first receive signals, and
      determine a second set of scan lines, each of which passes the moving object among the first set of scan lines based on the first receive signals, wherein the second set of scan lines includes a first scan line passing a first position in the moving object and a second scan line passing a second position in the moving object,
   wherein the probe is further configured to scan the second set of scan lines and a predetermined number of scan lines neighboring to the second set of scan lines, exclusive of other scan lines, and
   wherein the probe, when scanning the second set of scan lines, is further configured to scan the first scan line up to a first depth of the moving object at the first position and scan the second scan line up to a second depth of the moving object at the second position to form a first color Doppler image, the first depth and the second depth being different to each other depending on the first position and the second position in the moving object.

9. The system of claim 8, wherein the moving objects include a blood flow and a blood vessel.

10. The system of claim 8, wherein the image processor is further configured to form a second color Doppler image based on the first receive signals and a third color Doppler age by compounding the first and second color Doppler images.

11. The system of claim 8, wherein the second set of scan lines is denser than the first set of scan lines.

12. The system of claim 8, wherein the first set of scan lines is set to have a uniform scan line density.

13. The system of claim 8, wherein the first set of scan lines is set with different scan line densities.

14. The system of claim 13, wherein the first set of scan lines is set based on a possibility of existence of the moving object.

* * * * *